(12) United States Patent
Conn et al.

(10) Patent No.: US 6,997,864 B2
(45) Date of Patent: Feb. 14, 2006

(54) METHOD FOR OBTAINING DIAGNOSTIC INFORMATION RELATING TO A PATIENT HAVING AN IMPLANTED TRANSDUCER

(75) Inventors: Brian M. Conn, Broomfield, CO (US); Scott Allan Miller, III, Lafayette, CO (US); David L. Basinger, Loveland, CO (US)

(73) Assignee: Otologics, LLC, Boulder, CO (US)

( * ) Notice: Subject to any disclaimer, the term of this patent is extended or adjusted under 35 U.S.C. 154(b) by 148 days.

(21) Appl. No.: 10/700,188

(22) Filed: Nov. 3, 2003

(65) Prior Publication Data

US 2005/0096561 A1    May 5, 2005

(51) Int. Cl.
*H04R 25/00* (2006.01)
(52) U.S. Cl. ....................................................... 600/25
(58) Field of Classification Search .................. 600/25, 600/559; 73/585; 381/312–331; 181/126
See application file for complete search history.

(56) References Cited

U.S. PATENT DOCUMENTS

| | | | |
|---|---|---|---|
| 5,603,726 A | | 2/1997 | Schulman et al. |
| 5,833,626 A | * | 11/1998 | Leysieffer .................. 600/559 |
| 5,999,856 A | | 12/1999 | Kennedy |
| 6,264,603 B1 | | 7/2001 | Kennedy |
| 6,277,148 B1 | | 8/2001 | Dormer |
| 6,342,035 B1 | | 1/2002 | Kroll et al. |
| 6,554,762 B2 | | 4/2003 | Leysieffer |
| 2002/0026091 A1 | * | 2/2002 | Leysieffer .................... 600/25 |
| 2002/0048374 A1 | * | 4/2002 | Soli et al. ..................... 381/60 |

* cited by examiner

*Primary Examiner*—Samuel G. Gilbert
(74) *Attorney, Agent, or Firm*—Marsh Fischmann & Breyfogle LLP

(57) ABSTRACT

Method for obtaining diagnostic information utilizing an electrical signal output from an implantable transducer. According to one aspect of the invention, a method includes the steps of vibrating an ossicular bone of a patient having an implanted transducer using an input provided over a biological conduction path. The method further includes sensing in the implanted transducer an initial movement of the ossicular bone caused by the input and obtaining an electrical signal output from the implanted transducer generated in response to sensing the initial movement. The electrical signal output is then utilized to determine the diagnostic information.

43 Claims, 8 Drawing Sheets

METHOD FOR OBTAINING DIAGNOSTIC INFORMATION RELATING TO A PATIENT HAVING AN IMPLANTED TRANSDUCER

FIELD OF THE INVENTION

The invention is related to the field of hearing aids, and in particular, to methods for obtaining diagnostic information relating to a patient having a hearing aid that utilizes an implanted transducer.

BACKGROUND OF THE INVENTION

In the class of hearing aids generally referred to as implantable hearing aids, some or all of various hearing augmentation componentry is positioned subcutaneously on or within a patient's skull, typically at locations proximate the mastoid process. In this regard, implantable hearing aids may be generally divided into two sub-classes, namely semi-implantable and fully implantable. In a semi-implantable hearing aid, components such as a microphone, signal processor, and transmitter may be externally located to receive, process, and inductively transmit an audio signal to implanted components such as a transducer. In a fully implantable hearing aid, typically all of the components, e.g. the microphone, signal processor, and transducer; are located subcutaneously. In either arrangement, an implantable transducer is utilized to stimulate a component of the patient's auditory system.

By way of example, one type of implantable transducer includes an electromechanical transducer having a magnetic coil that drives a vibratory actuator. The actuator is positioned to interface with and stimulate the ossicular chain of the patient via physical engagement. (See e.g. U.S. Pat. No. 5,702,342). In this regard, one or more bones of the ossicular chain may be made to mechanically vibrate, causing the vibration to stimulate the cochlea through its natural input, the so-called oval window.

In the case of implantable transducers designed to interface with the ossicular chain, precise control of the engagement between the implantable transducer and the ossicular chain is important for proper transducer operation. For instance, stimulation of the ossicular chain, such as through vibration, relies at least in part on the appropriateness of the interface between the ossicular chain and transducer. Overloading or biasing of the implantable transducer relative to the ossicular chain can result in degraded performance of the biological aspect (movement of the ossicular chain) as well as degraded performance of the mechanical aspect (movement of the actuator). Similarly, if the implantable transducer is underloaded relative to the ossicular chain, e.g. a loose connection or no physical contact at all, vibrations may not be effectively communicated.

In this regard, at the time of implant, proper setup of an implantable transducer may depend on the present condition of the middle ear. For instance, the positioning of the transducer and the nature of the speech processing parameters may be determined based on patient specific biological aspects such as, damage or reduced mobility of the ossicular chain etc. Over time, however, such aspects may change, as well as, additional aspects may develop. These changes or developments, in turn, may affect the performance of the implanted transducer, e.g. such as by changing the engagement between the transducer and the ossicular chain.

In the field of audiometric screening and diagnosis, techniques have been designed to provide information relating to hearing function without active participation by a patient, such as may be desirable for infant patients. One such technique involves detection of transient evoked otoacoustic and/or otovibratory cochlear emissions in response to a resonant test signal provided to the patient. Otoacoustic emissions are sound pressure waves in a gaseous medium emitted from the cochlea. Similarly, otovibratory emissions are mechanical sound vibrations emitted from the cochlea. Such emissions are generated within the cochlea in response to a resonant acoustic stimulus after a latency period of typically 5–20 milliseconds.

SUMMARY OF THE INVENTION

In view of the foregoing, an object of the present invention is to simplify and improve implantation procedures for implantable transducers. A related object of the present invention is to improve the interfacing between an implantable transducer and an auditory component. In this regard, a related object of the present invention is to obtain diagnostic information relating to a patient utilizing an implantable transducer. For instance, such diagnostic information may include among other things, information relating to the interface between the implantable transducer and an auditory component, information relating to the implantable transducer, and/or information relating to the auditory system of the patient.

In the context of the present invention, the term biological component(s) refers to any natural biology of a patient. Similarly, the terms auditory component(s) and auditory system refer to the natural biological components of the hearing system of the patient. In contrast, the term hearing aid system refers to artificial components of a hearing aid, including an implantable transducer, that are provided to a patient to enhance the operation of the patient's biological auditory system.

In addressing the above-described problems, the present inventors have recognized that the above objectives may be achieved through a direct sensing of a movement, e.g. vibratory movement, of an auditory component, e.g. the ossicular chain, in response to an input provided to a patient over a biological conduction path. Furthermore, the present inventors have recognized that such directly sensed movements may be transduced into an electrical signal(s) that is/are indicative of diagnostic information. As noted diagnostic information may relate to, among other things, the relationship between the implanted transducer and ossicular chain, e.g. the interface between the same, information relating to the implantable transducer, and/or information relating biological aspects of a patient's auditory system.

In relation to implantable transducers according to the present invention, each of the various aspects discussed in more detail below includes a transducer capable of transducing mechanical energy into an electrical signal. According to one example, such an implantable transducer may include a body that is preferably constructed from a biocompatible material suitable for implantation within a patient. The implantable transducer may also generally include an actuator associated with the implantable transducer to stimulate an auditory component, e.g. the ossicular chain, to cause or enhance the sensation of sound for the patient. For instance, the actuator may be electrical, vibratory, and/or magnetic. In this regard, the implantable transducer may further include a transducer driver to drive the actuator in response to transducer drive signals. The driver may be, for example, an electrical, piezoelectric, electromechanical, and/or electromagnetic driver, etc.

In accordance with a first aspect of the present invention, a method for obtaining diagnostic information relating to a patient having an implantable transducer is provided. The method includes the step of vibrating an ossicular bone of a patient using an input test signal provided to the ossicular bone over a biological conduction path. In response to providing the input, the method includes the step of directly sensing an initial movement of the ossicular bone in the implanted transducer, and obtaining an electrical signal output from the transducer that is generated in response to the initial movement of the ossicular bone. Thereafter, the electrical signal output may be utilized to determine diagnostic information relating to the patient. In other words, according to the present method, the vibrating of the ossicular bone by the input test signal may occur substantially simultaneously to the sensing of the initial movement. To put it another way, the input test signal may occur at a first time interval and the sensing at a second time interval that at least partially overlaps the first time interval. In this regard, the sensed electrical signal output obtained from the transducer may be generated in response to the initial responsive movement of the ossicular bone moving an actuator of the implantable transducer. The mechanical movement of the actuator by the ossicular bone, is in turn, transduced into an electrical signal that is obtainable from the transducer.

In one feature of the present method, the vibrating step may include introducing an acoustic signal into an ear canal of the patient. The acoustic signal creates a sound pressure, which in turn, causes a natural deflection of the tympanic membrane. The deflection of the tympanic membrane, in turn, causes the natural mechanical response of the ossicular chain, e.g. deflection of the long process of the malleus. Advantageously, the movement of the ossicular chain, in response to the test signal, is transmitted directly to the implanted transducer, which in turn transduces the mechanical energy into the electrical signal output.

In another feature of the present method, the vibrating step may include mechanically stimulating the tympanic membrane, such as via, an apparatus placed in direct contact therewith, through the patient's ear canal. As with the former example, the deflection of the tympanic membrane through the mechanical stimulation causes a responsive movement of the ossicular chain to generate an electrical signal output at the transducer.

According to another feature of the present method, the vibrating step may include vibrating the bones of the skull. In particular, a bone vibrator or other means in contact with the patient's skull may be utilized to cause a vibrational movement of the skull and interconnected implanted transducer, relative to the ossicular chain. Such vibrational movement of the skull and interconnected transducer relative to the ossicular chain, in turn, causes a relative movement between the actuator and the interfaced ossicular chain, resulting in an electrical signal output at the transducer.

According to another feature of the present method, the utilizing step may include utilizing the electrical signal output to assess a relationship or interface between the ossicular bone and the implantable transducer. In this case, the assessment may include among other things, determining if a desired interface exists between the implantable transducer and the ossicular bone, or determining if the implantable transducer is underloaded relative to the ossicular bone, or determining if the implantable transducer is overloaded relative to the ossicular bone.

In view of the forgoing, the method may include repositioning the transducer relative to the ossicular chain of the patient in response to assessment of the interface therebetween. Such repositioning may include repositioning by an audiologist or other specialist using suitable instrumentation. In another embodiment, the repositioning may include an automatic repositioning performed by a positioning system incorporated into the hearing aid itself. In particular, such a positioning system is provided in co-owned U.S. patent application Ser. No. 10/083,181 that was filed on Feb. 26, 2002 and that is entitled "METHOD AND SYSTEM FOR POSITIONING IMPLANTED HEARING AID ACTUATORS." The entire disclosure of U.S. patent application Ser. No. 10/083,181 is incorporated herein by reference.

According to another feature of the present method, the utilizing step may include utilizing the electrical signal output to determine diagnostic information relating to the implantable transducer. For instance, in one approach the absence or presence of an electrical signal output from the implanted transducer may be indicative of the transducer operation. In another instance, it will be appreciated that for a given implanted actuator driven by a mechanical movement of an ossicular bone, which is in turn driven by a known input or test signal, the resulting electrical signal output should be within a predeterminable range during normal transducer operation. In this regard, characteristics of an electrical signal output for a malfunctioning transducer may be identified such that specific types of malfunctions are identifiable using the electrical signal output.

According to another feature of the present method, the utilizing step may include utilizing the electrical signal output to determine diagnostic information relating to a biological aspect of a patient's auditory system. For instance, the electrical signal output may be utilized to determine a mobility of the patient's ossicular chain. In this case, the determining step may further include using the determined mobility of the patient's ossicular chain to diagnose pathologies of the middle ear. Such pathologies may include without limitation, bony growths, arthritic conditions, and otitis media, etc.

According to another feature of the present method, the method may further provide for comparing the electrical signal output with a predetermined expected range of electrical signal outputs for a patient to generate the diagnostic information. In a further feature of the present method, the vibrating, sensing, obtaining, and utilizing steps may be repeated in connection with each of a plurality of patient assessments conducted as spaced timed intervals to obtain a corresponding plurality of comparison data. Such comparison data, in turn, may be utilized to generate the diagnostic information as a function of time.

According to another feature of the present method, the method may further include calculating one or more ratio comparisons of a parameter of the input test signal relative to a parameter of the response output electrical signal from the transducer. For instance, a ratio comparison of an input frequency to an output frequency from the implanted transducer may be made. Such ratios may be compared to optimal ratios to generate different diagnostic information. For instance, for a given direct articulation of the ossicular chain and interfaced actuator by an input, e.g. vibration, acoustic sound, mechanical stimulus of the tympanic membrane etc., an optimal ratio relative to a direct sensing of an output electrical signal may approach a one to one relationship for a linear system. Thus, according to one example, a lower ratio, e.g. measure of an input parameter relative to an output parameter at a given frequency, may be indicative of a better interface, mobility, etc. Additional aspects, advantages and applications of the present invention will be apparent to those skilled in the art upon consideration of the following description and drawings.

DETAILED DESCRIPTION

Reference will now be made to the accompanying drawings, which at least assist in illustrating the various pertinent features of the present invention. In this regard, the following description is presented for purposes of illustration and description and is not intended to limit the invention to the form disclosed herein. Consequently, variations and modifications commensurate with the following teachings, and skill and knowledge of the relevant art, are within the scope of the present invention.

Figure 1:
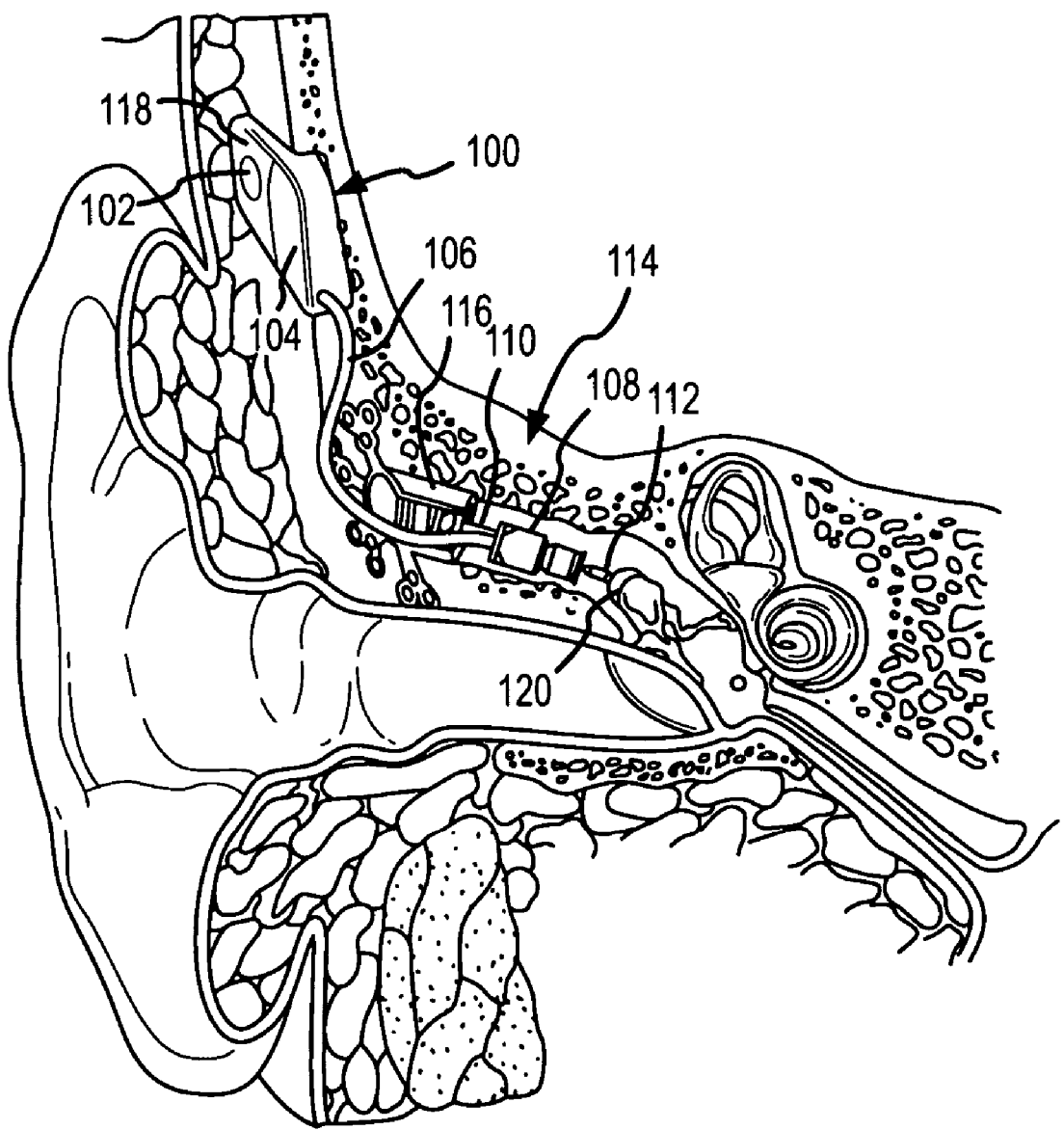
FIGS. 1 and 2 illustrate implantable and external componentry respectively, of a semi-implantable hearing aid device.
Figure 2:
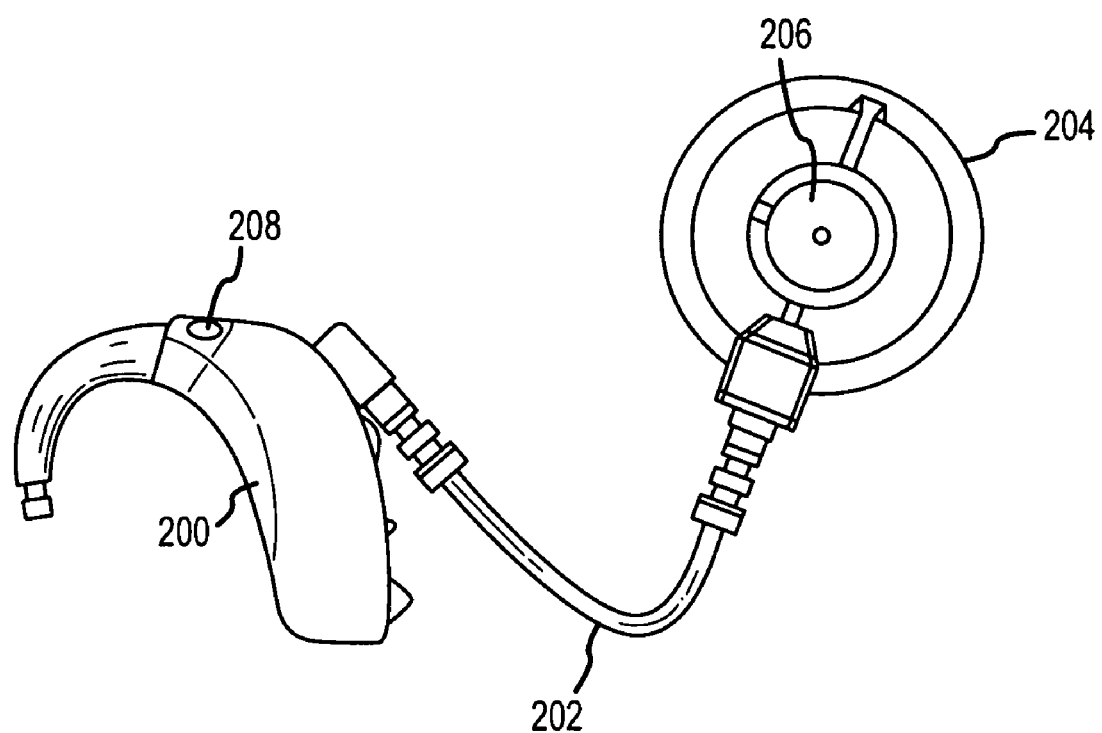

FIGS. 1 and 2 illustrate an example of a semi-implantable hearing aid system having implanted components shown in FIG. 1, and external components shown in FIG. 2. As will be appreciated, the present invention may also be employed in a substantially similar manner with a fully implantable hearing aid, wherein all components of a hearing aid system are located subcutaneously. Therefore, the following description is provided solely for the purpose of illustration and not limitation.

In the illustrated system, an implanted biocompatible housing 100 is located subcutaneously on a patient's skull. The housing 100 includes an RF signal transceiver 118 (e.g. comprising a coil element) and a signal processor 104 (e.g. comprising processing circuitry and/or a microprocessor). The signal processor 104 is electrically interconnected via wire 106 to a transducer 108. As will become apparent from the following description, various processing logic and/or circuitry may also be included in the housing 100.

The transducer 108 is supportably positioned in a mounting apparatus 116. The mounting apparatus 116 is attached to the patient's skull (e.g. via a hole drilled therein) typically within the mastoid process. The transducer 108 may be any type of transducer having the ability to transduce electrical inputs into mechanical outputs and vice versa. Some examples of the transducer 108 include without limitation electro-magnetic transducers, electromechanical transducers, piezoelectric transducers, etc.

For purpose of illustration, the transducer 108 will be described as an electro-magnetic transducer in the following description. In that regard, the transducer 108 includes an actuator 112, which according to this example, is designed to transmit axial vibrations to a member of the ossicular chain of the patient (e.g. the incus 120). The transducer 108 also includes a driver (not shown on FIG. 1) to drive the actuator 112 in response to transducer drive signals. According to the present electromagnetic transducer example, the driver may include a coil and one or more magnets configured to cause vibratory movement of the actuator 112 and stimulate the ossicular chain to produce or enhance the sensation of sound for the patient.

Referring to FIG. 2, the semi-implantable hearing aid system further includes an external housing 200 comprising a microphone 208 and internally mounted speech signal processing (SSP) unit (not shown). The SSP unit is electrically interconnected via wire 202 to an RF signal transceiver 204 (e.g. comprising a coil element). The external housing 200 is configured for disposition around the rearward aspect of the patient's ear. The external transceiver 204 and implanted receiver 118 each include magnets, 206 and 102, respectively, to facilitate retentive juxtaposed positioning.

During operation, acoustic signals are received at the microphone 208 and processed by the SSP unit within external housing 200. As will be appreciated, the SSP unit may utilize digital processing to provide frequency shaping, amplification, compression, and other signal conditioning, including conditioning based on patient-specific fitting parameters. In turn, the SSP unit via wire 202 provides RF signals to the transceiver 204. Such RF signals may comprise carrier and processed acoustic drive signal portions. The RF signals are then transcutaneously transmitted by the external transceiver 204 to the implanted transceiver 118. As noted, the external transceiver 204 and implanted transceiver 118 may each comprise coils for inductively coupling signals therebetween.

Upon receipt of the RF signals, the implanted signal processor 104 processes the signals (e.g. via envelope detection circuitry) to provide a processed drive signal via wire 106 to the transducer 108. According to this example, the drive signals cause the actuator 112 to vibrate at acoustic frequencies to effect the desired sound sensation via mechanical stimulation of the ossicular chain of the patient. As noted above, at least one factor related to proper operation of the transducer 108 is the interface between the actuator 112 and the ossicular chain. That is, if a desirable interface has been established, the actuator 112 will readily communicate axial vibrations to the ossicular chain of the patient. On the other hand, if the actuator 112 is "underloaded" (no interconnection or a less than desired connection has been established), axial vibrations may not be communicated or effectively communicated. Further, if the actuator 112 is "overloaded" against the ossicular chain, transmission may be adversely effected. For instance, the patient may experience sub-optimal stimulation via the transducer 108, including decreased sensitivity to the action of the transducer 108 or the perception of distortion or noise.

The present invention takes advantage of the principles of transducing mechanical energy into electrical energy and vice versa. As noted above, the transducer 108 transduces an electrical drive signal into mechanical vibrational movements of the actuator 112 to stimulate the ossicular chain, e.g. the incus 120, and cause or enhance the sensation of sound for the patient. Conversely, it will be appreciated that the application of a mechanical movement on the actuator 112 will generate a corresponding electrical signal in the transducer 108. In the case of a transducer, such as transducer 108, the electrical signal is generated by movement of the actuator 112 relative to the coil and/or magnet of the driver. This electrical signal may in turn be received from the transducer 108 and utilized to determine diagnostic information.

In one example according to this characterization, the diagnostic information may include information about the interface or engagement between the transducer 108 and the ossicular chain of the patient's auditory system. In particular, such information may include information relating to the amount of interfacing between the actuator 112 and an ossicular bone, such as the incus 120. In one example, the diagnostic information may indicate whether the transducer 108 is in contact with an ossicular bone, such as the incus 120. In another example, the diagnostic information may indicate a degree of contact between the transducer 108 and the ossicular bone. In this regard, the degree of contact generally refers to one of three conditions, namely: 1) a desired interface or contact between the transducer 108 and ossicular bone, 2) an overloaded or biased interface or contact between the transducer 108 and the ossicular bone, and 3) an underloaded or under biased interface or contact between the transducer 108 and the ossicular bone. It should be noted that the interface or contact between the transducer 108 and the ossicular bone referred to herein, may include among other things, an adjacent positioning of the actuator 112 relative to the ossicular bone, connection of the actuator 112 to the ossicular bone through a mechanical means such as a clamp, adhesive, etc., and/or connection of the actuator 112 to the ossicular bone through a means such as tissue or bone growth.

In another example according to the present characterization, the diagnostic information may further include information about the condition or function of various aspects of the patient's auditory system. For instance, the diagnostic information may include information indicative of the mobility of the ossicular chain. Such mobility diagnostic information, in turn, may be utilized to determine other diagnostic information, such as, pathologies of the ossicular chain, that are consistent with different determined motilities. For instance, a decreased mobility in the ossicular chain, as determined according to the present principles, may indicate pathologies including without limitation bony growths, arthritic conditions, and/or otitis media.

In another example according to the present characterization, the diagnostic information may further include diagnostic information relating to the implantable transducer 108. For instance, in one approach the absence or presence of an electrical signal output from the transducer 108 may be indicative of the transducer operation. In another instance, it will be appreciated that for a given actuator 112 driven by a mechanical movement of an ossicular bone, e.g. incus 120, which is in turn driven by a known input or test signal, the resulting electrical signal output should be within a predeterminable range during normal transducer operation. In this regard, characteristics of an electrical signal output for a malfunctioning transducer may be identified to indicate the same.

The movement of the actuator 112 relative to the coil and or magnet of the driver may be accomplished through direct articulation of an auditory component, e.g. the incus 120, interfaced with the actuator 112. In this regard, the natural responsive movement of the ossicular component to an input test signal may cause such direct articulation. It will be appreciated, in this regard, that the input test signal may be of numerous types and may be provided according to various methods. For purpose of illustration and not limitation, however, the following types of test signals and methods of generating and providing the same are provided.

In one example according to this characterization, the test signal may be provided to the patient and in particular to the middle ear via a biological conduction path. In the present context, a biological conduction path refers to a test signal conduction path comprising biological components. For instance, in one example of the biological conduction path the anatomical structures present in the ear canal and middle ear may be utilized to provide the test signal to the patient. For instance, a sound, preferably of short duration may be provided to the ear canal to cause sound pressure therein. The sound may be provided by, for instance, a speaker positioned proximate and external to the patient's ear or just inside the ear canal. The sound pressure, in turn, causes a natural deflection of the tympanic membrane, which in turn, causes the natural mechanical response of the ossicular chain, e.g. deflection of the long process of the malleus. The movement of the ossicular chain in response to the test signal, or sound pressure, is transmitted directly to the transducer 108, and specifically to the interconnected actuator 112, which in turn transduces the mechanical energy into an electrical signal output.

In another example, that also utilizes the anatomical structures of the ear canal and middle ear, the tympanic membrane may be mechanically stimulated, such as via, an apparatus placed in direct contact therewith, through the patient's ear canal. As with the former example, the deflection of the tympanic membrane through the mechanical stimulation causes a responsive movement of the ossicular chain and interfaced actuator 112 to generate an electrical signal output at the transducer 108.

In anther example according to this characterization, the bones of the skull may be utilized to provide the test signal. In particular, a bone vibrator or other means in contact with the patient's skull may be utilized to cause a vibrational movement of the skull and interconnected transducer 108, relative to the ossicular chain. Such vibrational movement of the skull and interconnected transducer 108 relative to the ossicular chain, will in turn, cause a relative movement between the actuator 112 and the interfaced incus 120, resulting in an electrical signal output at the transducer 108.

A particular advantage of the present invention that will be appreciated by those skilled in the art is that in each of the above examples, the electrical signal output from the transducer 108 results from detecting an initial movement of an ossicular bone, e.g., incus 120, in response to its stimulation by the input test signal. Characterized another way, the input test signal may be provided to the patient at a first time interval and the output electrical signal sensed at a second time interval. In this regard, the second time interval at least partially overlaps the first time interval such that a substantially simultaneous stimulation and sensing of movement occurs. In other words, a substantially simultaneous stimulation of the ossicular bone, and sensing of the electrical signal output is accomplished.

This in turn provides the advantage of reducing distortion in the electrical signal output by minimizing delay between when the input test signal is provided and when the electrical signal output is detected. In this regard, signal distortion refers to any departure of a response electrical signal's waveform from that which should result from an input test signal's waveform. Such distortion may be caused by numerous variables such as the frequency response of other portions of the auditory system e.g. cochlear emissions. Advantageously, the present invention reduces the amount that the input test signal may be operated on by the auditory system (e.g. distortion) through the direct detection or sensing of the initial responsive movement of the ossicular chain.

Still yet another advantage of the present invention, is that because distortion is reduced through direct sensing of the initial movement of the ossicular chain, distortion in the electrical signal output may be utilized to generate desired diagnostic information. According to this characterization, if a proper interface exists between the actuator 112 and the incus 120, the electrical signal output should contain little or very little distortion. Thus, distortion, such as on a periodic basis, in the electrical signal output may indicate an underloaded interface condition, wherein the periodic distortion results from an under biased, e.g. loose connection, between the actuator 112 and incus 120. Likewise, distortion, such as on a continuous basis, may indicate an overloaded interface condition, as movement of the incus 120 will be constrained by the over biased actuator 112 thereby distorting the electrical output generated in response to the test signal input.

Figure 3:
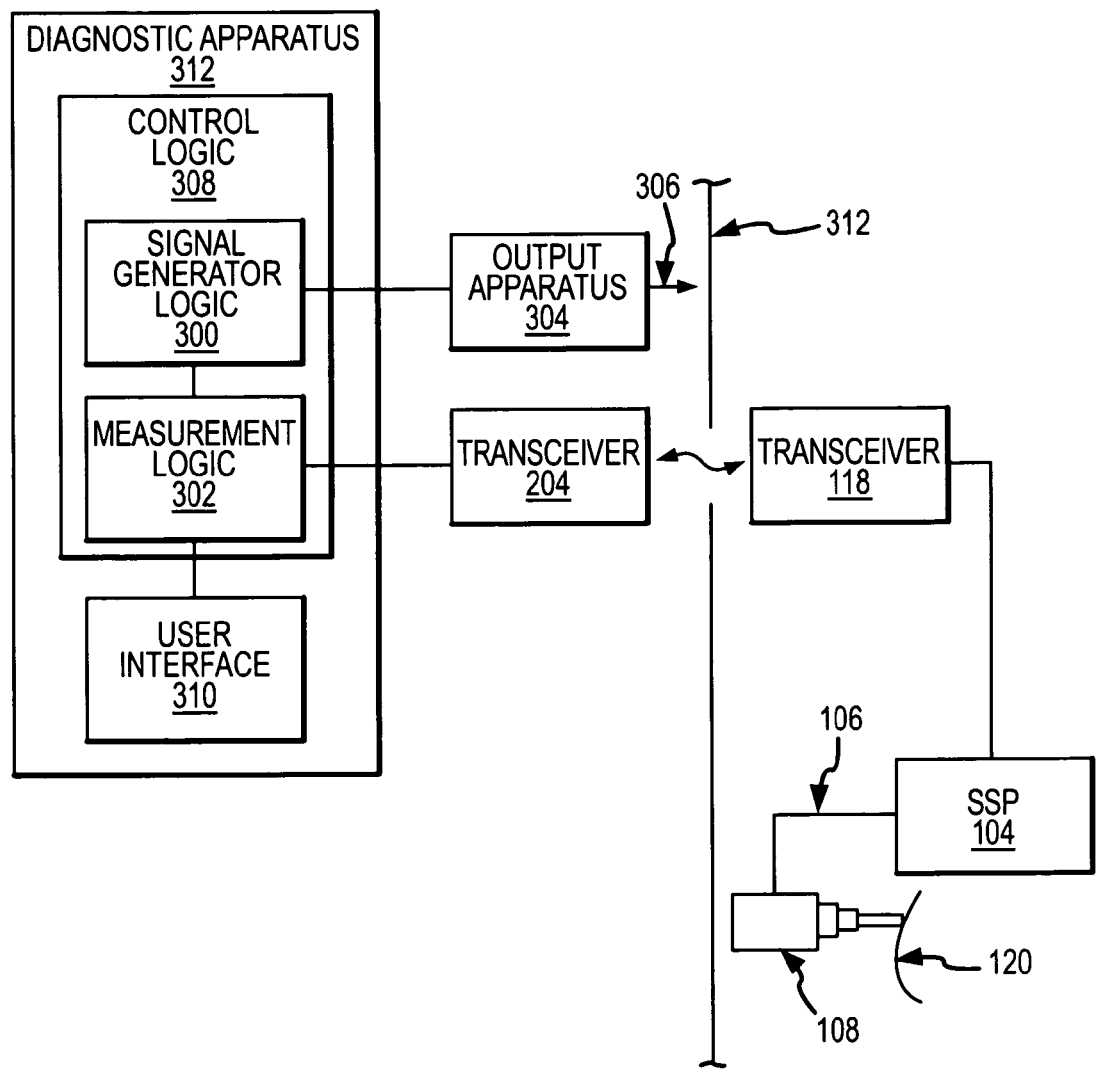
FIG. 3 illustrates a schematic view of a hearing aid system and diagnostic apparatus.

FIG. 3 illustrates a schematic view of the hearing aid of FIGS. 1 and 2 in combination with a diagnostic apparatus 312 and test signal output apparatus 304. The diagnostic apparatus 312 includes a user interface 310 and control logic 308. The control logic 308 includes signal generator logic 300 and measurement logic 302. The control logic 308 is in communication with the output apparatus 304, the user interface 310, and the transceiver 204 of the hearing aid system. In particular, according to one example, the signal generator logic 300 is in communication with the output apparatus 304 while the measurement logic 302 is in communication with the external transceiver 204.

According to this characterization, the communication link between the signal generator logic 300 and the output apparatus 304 as well as the communication link between the measurement logic 302 and the transceiver 204 may be a wireless link or a physical wireline link. In the latter case, where the communication link between the measurement logic 302 and the transceiver 204 is a wireline link, it is preferred that a detachable connection be provided with the transceiver 204. Such a connection may be made for example via a conventional audio input/output jack that permits temporary connection of the transceiver 204 to the diagnostic apparatus 312 and specifically to the measurement logic 302 during a diagnostic operation.

A diagnostic operation includes providing an input test signal 306 and obtaining a response from the transducer 108. In this regard, a transducer response may include, among other things, the above-described electrical signal output, as well as the lack of any detectable response. In other words, as will be apparent from the following description, the lack of an electrical signal output may be indicative of certain desired diagnostic information. Furthermore, as will be appreciated from the following description, a diagnostic operation may be performed on a periodic basis by an audiologist or other specialist, or may be performed by the hearing aid itself during a self-analysis initiated by the hearing aid's programming logic. It will also be appreciated from the following description, that during a diagnostic operation, the microphone 208 of the hearing aid may be temporarily turned off to prevent detection of other sound sources that may interfere with the diagnostic operation.

The signal output apparatus 304 may be any device or group of devices configured to provide the input test signal 306 to a patient. As noted, the input test signal 306 may take numerous forms and therefore so may the signal output apparatus 304. For instance, in one example, the signal output apparatus 304 may be the above discussed bone vibrator while the input test signal 306 may be a vibratory signal provided to the patient's skull. In another example, the output apparatus 304 may be a speaker and the input test signal 306 may be a tone, provided to the patient's ear canal. In this regard, the tone may have predetermined characteristics, with some examples including without limitation, a "chirp" a "click" and/or a sound wave provided at a desired frequency or over a desired frequency range. In another example, the output apparatus 304 may be a transducer similar to the transducer 108 that has been modified such that it is insertable into the ear canal of the patient to mechanically stimulate the tympanic membrane and cause the implanted transducer 108 to provide the electrical signal output.

The signal generator logic 300 may be any logic configured to cause the output apparatus 304 to produce the input test signal 306. Therefore, it will be appreciated that the signal generator logic 300 may be a part of the diagnostic apparatus 312, as depicted on FIG. 3, or alternatively may be a part of the output apparatus 304. According to this characterization, the signal generator logic 300 may be configured to cause the output apparatus 304 to produce test signals of different predetermined characteristics. Such characteristics may be designed to generate information in the form of electrical signal outputs from the transducer 108 that are indicative of different diagnostic information. In this regard, the signal generator logic 300 may also provide the test signal characteristics to the measurement logic 302 for comparison of the test signal characteristics with the induced electrical signal output from the transducer 108.

The measurement logic 302 may be any logic configured to receive a response from the transducer 108 and utilize the response to generate diagnostic information. As noted above, a transducer response may include, among other things, the above-described electrical signal output, as well as the lack of a detectable response from the transducer 108. Accordingly, in one embodiment of the invention, the lack of a response in the transducer 108 upon providing the input test signal 306 may indicate, among other things, at least one of three potential issues. First, the lack of a response may indicate a lack of an interface or contact between the transducer 108 and the desired ossicular bone, e.g., incus 120. Second, the lack of a response may indicate an operational problem with the transducer 108. Finally, the lack of a response may indicate a severely overloaded condition between the transducer 108 and the desired ossicular bone, such that stimulation of the ossicular bone by the test signal and the resulting electrical signal output from the transducer 108 is impossible.

According to another feature, the measurement logic 302 may be configured to process an electrical signal output to generate an output indicative of a degree of interfacing or contact between the transducer 108 and an ossicular bone, such as the incus 120. For example, the output may indicate if: 1) a desired interface condition exists; 2) an overloaded interface condition exists; or 3) an underloaded interface condition exists. It will be appreciated in this regard, that the desired interface condition may vary as a function of the transducer type and design. Thus, in the present context, an overloaded interface condition includes any condition wherein the transducer 108 is biased more than a desired amount relative to the ossicular bone. Similarly, an underloaded condition includes any condition other than a desired interface condition and an overloaded condition, including a no interface condition, e.g. where the transducer 108 is not contacting the desired ossicular bone.

According to another feature, the measurement logic 302 maybe configured to use different characteristics of the electrical output signal from the transducer 108 to identify conditions present in a patient. For instance in one particular example of such operation, the measurement logic 302 may compare the amount of distortion present or absent in a particular output signal to identify the different conditions. In this regard and as noted above, if a proper interface exists between the actuator 112 and the incus 120 the output signal from the transducer 108 preferably contains little or very little distortion, such that, periodic distortion may indicate an underloaded interface condition and continuous distortion may indicate an overloaded interface condition.

According to another feature, the measurement logic 302 may utilize an electrical signal output from the transducer 108 to generate an output indicative of the mobility of the middle ear ossicular chain. For instance, the ossicular mobility may be characterized by a comparison of the electrical signal output amplitude with a predetermined expected range for a patient utilizing a similar transducer with normal ossicular mobility. In this case, an electrical signal output that is outside of the range would indicate a decreased mobility. In another example, the mobility may be characterized by repeatedly measuring the electrical signal output from the transducer 108 in response to repeated test signals 306. In this case, a decrease in the electrical signal output amplitude over repeated measurements may be indicative of decreased mobility of the ossicular chain. Similarly, an increase in the electrical signal output amplitude over repeated measurements may be indicative of a disarticulation of one or more of the ossicular bones.

As noted above, a particular advantage of such information is that the mobility diagnostic information may further be utilized to diagnose certain pathologies, e.g. bony growths, arthritic conditions, otitis media etc., of the ossicular chain that are consistent with changes in mobility. Also advantageously, the mobility information may be utilized to determine changes in certain pathologies in a patient over time. For example, if it is known that a patient suffers from an arthritic condition, then current mobility diagnostic information may be compared with past data to determine changes in the patient's condition over time. Similarly, such information may be utilized not only to determine a change, but also to determine a rate of change, which in turn may be utilized in other ways, such as, for example, determining the effectiveness of a particular treatment.

Operationally, the measurement logic 302 may perform various functions. For instance, the measurement logic 302 may make comparisons of the electrical signal output from the transducer 108 to the input test signal 306 to determine which one of the above described interface conditions exist. According to this characterization, the comparisons may include a graphical display of the two signals on the user interface 310. Alternatively, the comparisons may include other operations such as determining a degree of over or under loading, or a degree of mobility that exists, and providing an indication of the same to the user interface 310.

In yet another example, the measurement logic 302 may a calculate ratio(s) at different frequencies between the input test signal and the output electrical signal. Such ratios may be compared to optimal ratios to generate different diagnostic information according to the present invention. For example, it is known that for a non-linear system, such as the auditory system, an input to output ratio will vary over a given frequency range. In this regard, input/output ratios at lower frequencies are considerably different from that of similar input/output ratios at higher frequencies. Therefore, ratio comparisons may be made over a given frequency range to identify conditions known to affect the hearing function in such a range. For instance, comparisons may be made at lower frequencies to diagnosis certain conditions, such as infections, whereas comparisons may be made at higher frequencies to diagnose other conditions, such as arthritic conditions.

In another example, which assumes the transducer 108 and interfaced ossicular bone are a linear system, or can be made to resemble a linear system, an optimally interfaced transducer 108 will generate a scaled copy of the input test signal 306 without additional frequency components. For instance, for a given direct articulation of the ossicular chain and interfaced actuator 112 by an input test signal, an optimal ratio relative to a direct sensing of an output electrical signal may approach a one to one relationship for a linear system. Thus, according to one example, a lower ratio, e.g. measure of an input parameter relative to an output parameter at a given frequency, may be indicative of a better interface, mobility, etc. In other words, a magnitude component of the electrical signal output may be utilized to assess the interface. In particular, a reduced magnitude relative to an electrical signal output generated by a properly interfaced transducer would be indicative of an overloaded interface. In addition, the amount of magnitude reduction is a function of the amount of loading such that an audiologist or other specialist is further provided with information on an amount of adjustment required to properly interface the transducer 108. An underloaded interface, on the other hand, may be indicated by an output electrical signal exhibiting inter-modulation distortion, harmonic distortion, low and/or no electrical signal output. As noted above, the complete lack of an electrical signal output from the transducer 108 could indicate either a severely overloaded condition or a severely underloaded condition. In other words, if the transducer 108 is loaded such that the actuator 112 is not movable, even in response to stimulation of the ossicular bone, no electrical signal output will be generated. Likewise, the electrical signal output may not be generated where no contact exists between the actuator 112 and the ossicular bone.

It will be appreciated that the above-described electrical signal outputs for a linear system and their indicated conditions, are provided to illustrate the principles of the present invention. It will also be appreciated, that other signal outputs indicating different conditions exist as a function of a particular transducer design. Furthermore, the particular transducer design at least affects, if not dictates, the meaning and type of a particular electrical signal output(s), which is predeterminable based on the particular transducer design.

As noted, the output of the measurement logic 302 is provided to the user interface 310. In this regard, the user interface 310 may include an output device such as a monitor and an input device such as a keyboard or other means for providing inputs to the control logic 308. According to this characterization, the control logic 308 controls operation of the diagnostic apparatus 312. For instance, the control logic 308 may process user inputs to control operation of the signal generator logic 300 to cause output apparatus 304 to produce an input test signal 306 having specific desired characteristics. The control logic 308 may also control operation of the measurement logic 302 during the generation and display of the various types of diagnostic information. Accordingly, the user interface 310 provides a means for an audiologist or other operator to control a data acquisition event and generate different desired diagnostic information.

It will be appreciated that the above described control logic 308 including the signal generator logic 300 and measurement logic 302 could comprise instructions that are stored on a storage media. The instructions could be retrieved and executed by a processor. Some examples of instructions are software, program code, and firmware. Some examples of storage media are memory devices, tape, disks, integrated circuits, and servers. The instructions are operational when executed by the processor to direct the processor to operate in accord with the invention. The term "processor" refers to a single processing device or a group of inter-operational processing devices. Some examples of processors are integrated circuits and logic circuitry. Those skilled in the art are familiar with instructions, processors, and storage media.

Figure 4:
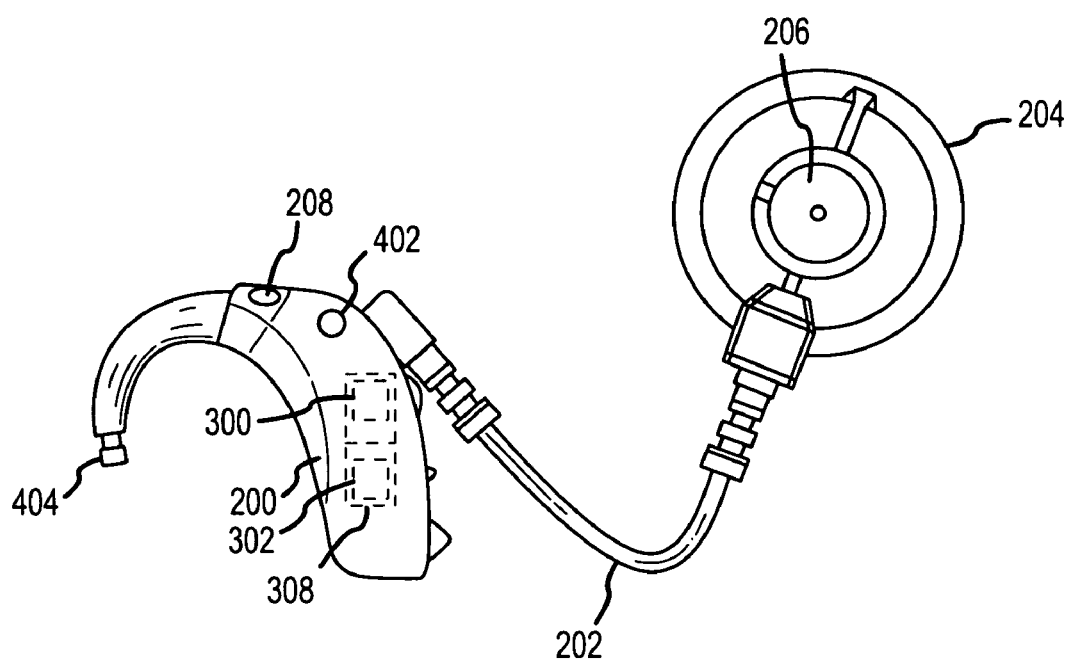
FIG. 4 illustrates an alternative example of the external componentry of the hearing aid of FIG. 1.

With reference to FIG. 4, in another embodiment of the present invention, the control logic 308 including the signal generator logic 300 and measurement logic 302 may be incorporated into the processing logic of the hearing aid system. According to this characterization, the control logic 308 may be operational to periodically perform a data acquisition event and store obtained data in memory for later downloading by an audiologist or other operator. In this regard, the external componentry may further include a data port 402 for connecting and downloading information from the hearing aid for analysis by an audiologist. Further, in this regard, the external componentry may include a speaker 404 operational under direction of the signal generator logic 302 to provide the test signal/tone 306 to the ear canal when the external componentry is disposed about the reward aspect of the patient's ear.

Operationally, the control logic 308 may be configured to perform a data acquisition event at any time. Do to factors such as patient inconvenience, however, it may be desirable to perform the test when the hearing aid is switched "on" and/or "off." In this case, the control logic 308 may temporarily prevent operation of the microphone 208, upon detecting that the hearing aid is switched on. During this temporary delay, a test signal/tone 306 and electrical signal output may be provided and received back in the control logic 308. Similarly, upon detecting that the hearing aid is switched off the control logic 308 may perform a similar operation before completely powering off.

Figure 5:
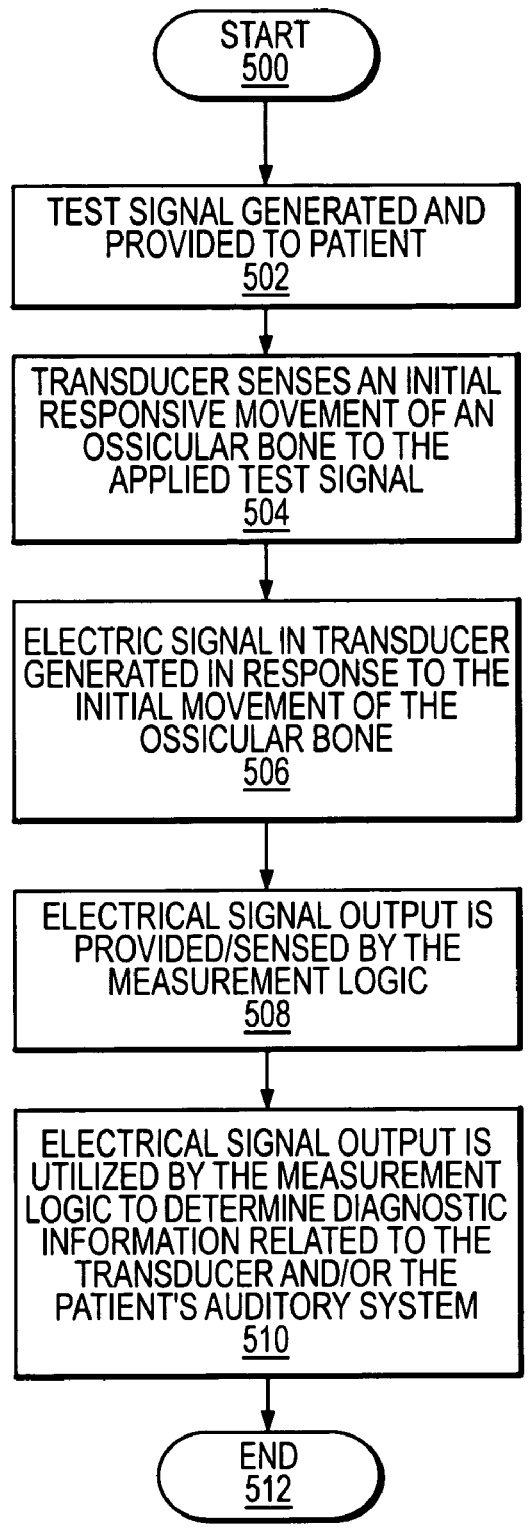
FIG. 5 is a flow chart illustrating one example of an operational protocol for obtaining diagnostic information relating to a patient having an implanted transducer.

FIG. 5 illustrates one example of an operational protocol according to the present invention. The operational protocol of FIG. 5 begins at step 500. At step 502, an input test signal 306 is generated under the direction of the signal generator 300 and provided to the patient. The input test signal 306 may be provided to the patient according to any of the above examples. For instance, the input test signal 306 may be provided by the output apparatus 304 and may be in the form of a tone, a mechanical stimulation, or a vibratory stimulation of the auditory system over a biological conduction path. In another instance, the test signal may be provided by the hearing aid system itself via a self-analysis as described above.

Substantially simultaneous to the provision of the input test signal 306, the transducer 108 senses a movement of an ossicular bone caused by the applied test signal, at step 504. At step 506, the movement of the actuator 112 generates an electrical signal output in the transducer 108. At step 508, the electrical signal output is provided/sensed by the measurement logic 302 e.g. via the transceiver 204. At step 510, the electrical signal output is utilized by the measurement logic 302 to determine diagnostic information related to the transducer 108 and/or the patient's auditory system and the same is provided to the user interface 310. The operation ends at step 512.

In another embodiment of the present invention, the interface between the transducer 108 and the ossicular bone may be adjusted upon a determination that a condition other than a desired interface exists. In one embodiment according to this characterization, such adjustment may include manual repositioning. It will be appreciated that such manual adjustment may be performed during an implantation procedure to properly locate and interface the transducer 108 to an ossicular bone. Alternatively, it may be performed at any time, wherein an automatic positioning system is incorporated into the hearing aid system itself. An example of such a positioning system is provided in co-owned U.S. patent application Ser. No. 10/083,181 that was filed on Feb. 26, 2002 and that is entitled "METHOD AND SYSTEM FOR POSITIONING IMPLANTED HEARING AID ACTUATORS." Those skilled in the art will appreciate the particular advantages provided where this embodiment is combined with the self-analysis embodiment such that the hearing aid system may assess the interface of the transducer 108 with the ossicular bone and automatically perform compensatory repositioning in the event of an undesired interface.

Figure 6:
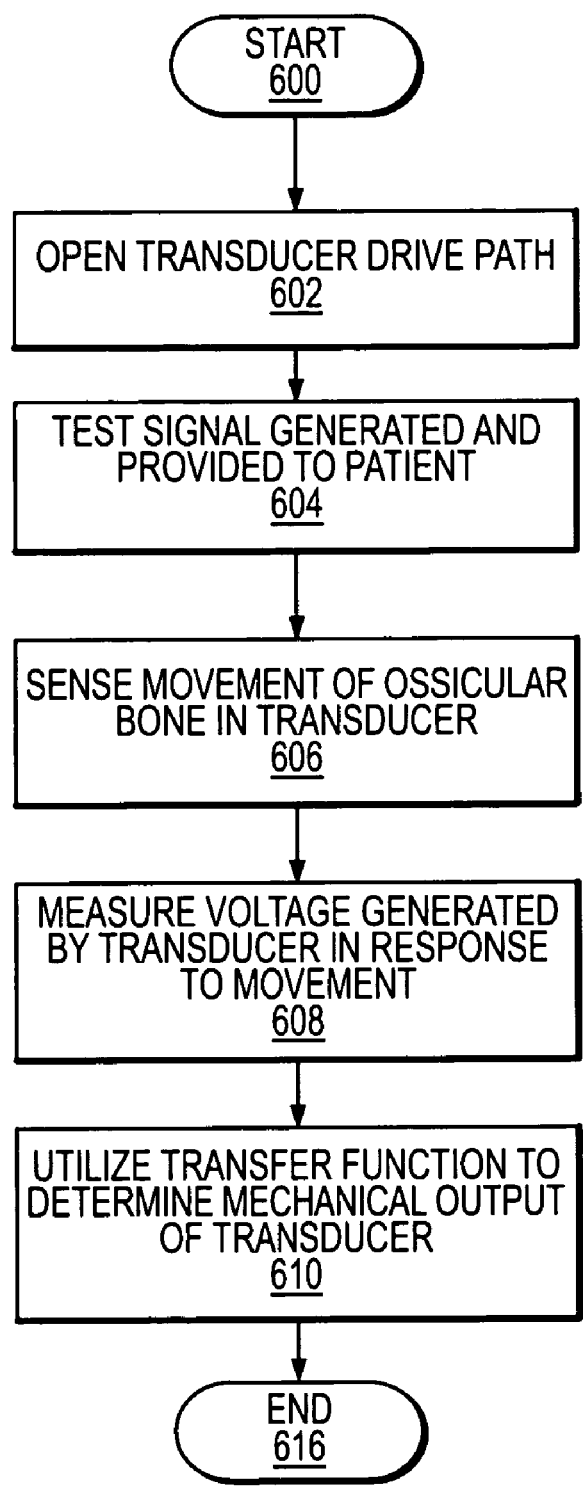
FIG. 6 is another flow chart illustrating another example of an operational protocol obtaining diagnostic information relating to a patient having an implanted transducer.

FIG. 6 illustrates another example of an operational protocol according to the present invention. In this example, the transfer function of the implantable transducer 108 is utilized to calculate responsive mechanical movement of the actuator 112, e.g. a velocity, for a given magnitude of an input test signal 306. In this regard, it will be appreciated that the transducer transfer function relates the magnitude of an input drive signal and the mechanical movement or velocity of the actuator 112 generated by the given magnitude of the drive signal. In other words, the transfer function may be utilized to determine the mechanical output generated for a given magnitude of electrical input.

On FIG. 6 the operation begins at set 600. At step 602, a transducer drive path over wire 106 is opened to prevent power from being applied to the transducer 108 during the test event, e.g. resulting from audio signals detected by the microphone 208. At step 604 an input test signal 306 having a predetermined magnitude or voltage is generated and provided to the patient's middle ear, over a biological conduction path and under the direction of the signal generator 300. As with the above examples, the input test signal 306 may be in the form of a sound, a vibration and/or mechanical stimulation of the tympanic membrane, etc. Substantially simultaneous to the provision of the input test signal 306, the transducer 108 senses a movement of an ossicular bone caused by the applied test signal, at step 606. At step 608, an electrical signal output and, in particular, a voltage of the electrical signal output is measured. At step 610, the transducer transfer function may be utilized by the measurement logic 302 to determine the velocity of the actuator 112, realized in response to the given input test signal 306. Operation ends at step 612.

In this regard, it will be appreciated that the measured voltage of the output electrical signal from the transducer 108 is proportional to the velocity of the actuator 112 such that the measured voltage is indicative of the amount of loading between the actuator 112 and the ossicular chain. Similarly, it will be appreciated that such voltage measurements may be compared to predetermined output voltages for a properly interface transducer, such that a degree of over or under loading is determinable. For instance, loudness growth curves may provide a useful comparison of the actuator velocity or motion in response to a given magnitude for the input test signal 306. Further, in this regard, it will be appreciated that where it is known that a desired interface exists between the transducer 108 and ossicular bone, e.g. incus 120, the measured voltage may be indicative of ossicular mobility and utilized as described above to diagnose patient pathologies.

Figure 7:
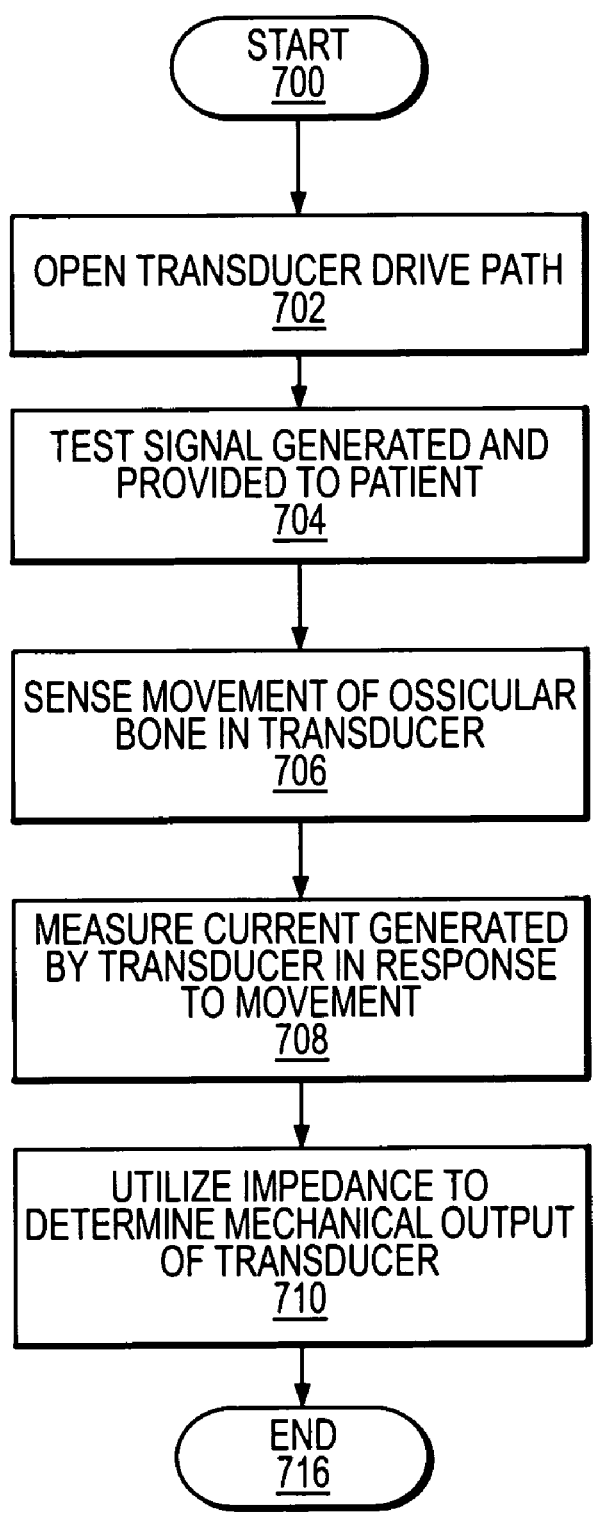
FIG. 7 is another flow chart illustrating another example of an operational protocol obtaining diagnostic information relating to a patient having an implanted transducer.
Figure 8:
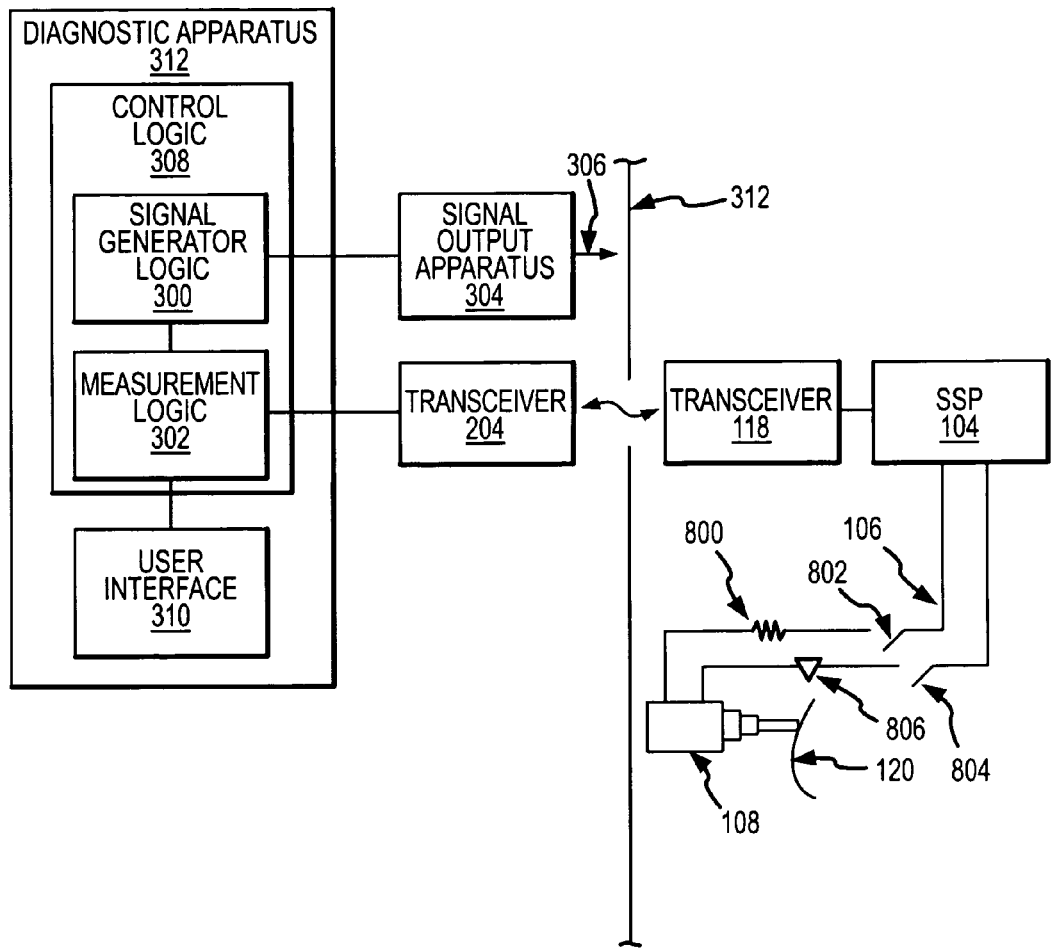
FIG. 8 illustrates another schematic view of a hearing aid system and diagnostic apparatus.

FIG. 7 illustrates another example of an operational protocol according to the present invention. The protocol of FIG. 7 is similar to that of FIG. 6, except that a current of the output electrical signal from the transducer 108 is measured, rather than a voltage. In this regard, the protocol of FIG. 7 begins at step 700. At step 702, a transducer drive path over wire 106 is opened to prevent power from being applied to the transducer 108. At step 704, an input test signal 306 is generated and provided to the patient via a bone conduction path and under the direction of the signal generator 300. As with the previous example, the input test signal 306 may be an audio signal, a vibration or mechanical stimulation provided to the middle ear. At step 706, the transducer 108 and, in particular, the actuator 112 senses an initial movement of the ossicular chain in response to the applied input test signal 306. At step 708, an electrical signal output and, in particular, a current is measured. In this regard, the current may be measured according to any appropriate means. For instance, the current may be measured using a sense resistor 800 as illustrated in FIG. 8. According to this example, a safety switch 802 may be provided to open the transducer drive path at step 602. Furthermore, a switch 804 may be provided to provide the output electrical signal to an amplifier 806 and ultimately the measurement logic 302.

At step 710, a velocity of the actuator 112 driven by the ossicular chain in response to the input test signal 306 may be calculated using the impedance of the transducer 108. In other words, the transducer impedance, which relates the voltage and current, may be utilized to obtain the voltage of the electrical signal output, which is proportional to the velocity of the actuator 112. Thus, as with the above example, the interface between the transducer 108 and ossicular bone may be assessed. Alternatively, ossicular mobility and pathologies present in a patient may be identified as well according to the present principles. The operation ends at step 712

The descriptions provided above are for exemplary purposes only and are not intended to limit the scope of the present invention. Various modifications and extensions of the described embodiments will be apparent to those skilled in the art and are intended to be within the scope of the invention as defined by the claims that follow.

What is claimed:

1. A method for obtaining diagnostic information relating to a patient having an implanted transducer, comprising:
    vibrating an ossicular bone of the patient using an input provided to the ossicular bone over a biological conduction path, wherein the biological conduction path consists of biological components of the patient, and wherein said input is not provided by said implanted transducer;
    sensing in the implanted transducer an initial movement of the ossicular bone caused by the input provided over the biological conduction path;
    obtaining an electrical signal output from the implanted transducer generated in response to sensing, in the implanted transducer, the initial movement of the ossicular bone; and,
    utilizing the electrical signal output to determine the diagnostic information relating to the patient.

2. A method as recited in claim 1, wherein the vibrating and sensing steps comprise:
    vibrating the ossicular bone during a first time interval and sensing the initial movement during a second time interval, wherein the first and second time interval at least partially overlap.

3. A method as recited in claim 1, wherein the vibrating and sensing steps comprise:
    vibrating the ossicular bone and sensing the initial movement substantially simultaneously.

4. A method as recited in claim 1, wherein the utilizing step comprises:
    utilizing the electrical signal output to determine fitting parameter diagnostic information relating to at least one fitting parameter for the implanted transducer.

5. A method as recited in claim 4, wherein the at least one fitting parameter includes an interface between the implanted transducer and the ossicular bone and the utilizing step comprises:
    assessing the interface between the ossicular bone and the implanted transducer.

6. A method as recited in claim 5, wherein the assessing step comprises:
    determining if the implanted transducer is underloaded relative to the ossicular bone.

7. A method as recited in claim 5, wherein the assessing step comprises:
    determining if the implanted transducer is overloaded relative to the ossicular bone.

8. A method as recited in claim 5, wherein the assessing step comprises:
    determining if a desired interface exists between the implanted transducer and the ossicular bone.

9. A method as recited in claim 5, further comprising:
    repositioning the transducer relative to the ossicular bone in response to the assessing step.

10. A method as recited in claim 1, wherein the utilizing step comprises:
    utilizing the electrical signal output to determine diagnostic information that relates to the operation of the implanted transducer.

11. A method as recited in claim 10, wherein the implanted transducer diagnostic information includes at least one operating parameter of the implanted transducer.

12. A method as recited in claim 11, wherein the at least one operating parameter includes a transducer performance parameter.

13. A method as recited in claim 1, wherein the utilizing step comprises:
    utilizing the electrical signal output to determine auditory system diagnostic information relating to the patient's auditory system.

14. A method as recited in claim 13, wherein the auditory system diagnostic information includes a mobility of the patient's ossicular chain.

15. A method as recited in claim 14, the method comprising:
    using the mobility of the patient's ossicular chain to diagnose pathologies of the middle ear.

16. A method as recited in claim 15, wherein the pathologies are selected from the group of pathologies comprising: bony growths, arthritic conditions, and otitis media.

17. A method as recited in claim 1, wherein the vibrating step includes:

introducing an acoustic signal into an ear canal of the patient.

18. A method as recited in claim 1, wherein the vibrating step comprises:
vibrating at least a portion of a skull of the patient.

19. A method as recited in claim 1, wherein the vibrating step comprises:
mechanically stimulating the tympanic membrane of the patient.

20. A method as recited in claim 1, wherein the electrical signal output is generated in response to movement of an actuator of the implanted transducer by the ossicular bone.

21. A method as recited in claim 20, wherein the sensing step comprises:
transducing the movement of the actuator into the electrical signal output.

22. A method as recited in claim 1, wherein the utilizing step comprises:
comparing the electrical signal output with a predetermined electrical signal output to generate the diagnostic information.

23. A method as recited in claim 1, wherein the utilizing step comprises:
comparing the electrical signal output with a predetermined range of electrical signal outputs to generate the diagnostic information.

24. A method as recited in claim 1, wherein the utilizing step comprises:
calculating a ratio between the input and the electrical signal output; and
comparing the ratio to a predetermined ratio to generate the diagnostic information.

25. A method as recited in claim 1, wherein the utilizing step comprises:
obtaining at least one signal value from the electrical signal output; and
comparing the at least one signal value with a corresponding predetermined value to obtain comparison data, wherein the comparison data is indicative of the diagnostic information.

26. A method as recited in claim 25, wherein the at least one value corresponds with a magnitude component of the electrical signal output.

27. A method as recited in claim 26, wherein the input comprises at least one component of a predetermined frequency, and wherein the magnitude component of the electrical signal output is obtained in corresponding relation to the predetermined frequency of the input component.

28. A method as recited in claim 25, wherein the at least one value corresponds with a flow component of the electrical signal output.

29. A method as recited in claim 1, further comprising:
repeating the vibrating, sensing, obtaining, and utilizing steps in connection with each of a plurality of patient assessments conducted as spaced timed intervals to obtain a corresponding plurality of comparison data; and
utilizing the plurality of comparison data to generate the diagnostic information as a function of time.

30. A method for obtaining diagnostic information relating to a patient having an implanted transducer, comprising:
vibrating an ossicular bone of the patient using an input provided to the ossicular bone over a biological conduction path, wherein the biological conduction path consists of biological components of the patient;
sensing in the implanted transducer an initial movement of the ossicular bone caused by the input provided over the biological conduction path;
obtaining an electrical signal output from the implanted transducer generated in response to sensing, in the implanted transducer, the initial movement of the ossicular bone; and,
utilizing the electrical signal output to determine diagnostic information that relates to the operation of the implanted transducer.

31. A method as recited in claim 30, wherein the diagnostic information includes at least one operating parameter of the implanted transducer.

32. A method as recited in claim 31, wherein the at least one operating parameter includes a transducer performance parameter.

33. A method for obtaining diagnostic information relating to a patient having an implanted transducer, comprising:
vibrating an ossicular bone of the patient using an input provided to the ossicular bone over a biological conduction path, wherein the biological conduction path consists of biological components of the patient, wherein said input is not provided by said implanted transducer;
sensing in the implanted transducer an initial movement of the ossicular bone caused by the input provided over the biological conduction path;
obtaining an electrical signal output from the implanted transducer generated in response to sensing, in the implanted transducer, the initial movement of the ossicular bone; and,
utilizing the electrical signal output to determine auditory system diagnostic information relating to the patient's auditory system, wherein the auditory system diagnostic information includes a mobility of the patient's ossicular chain.

34. A method as recited in claim 33, the method comprising:
using the mobility of the patient's ossicular chain to diagnose pathologies of the middle ear.

35. A method as recited in claim 34, wherein the pathologies are selected from the group of pathologies comprising: bony growths, arthritic conditions, and otitis media.

36. A method for obtaining diagnostic information relating to a patient having an implanted transducer, comprising:
vibrating an ossicular bone of the patient using an input provided to the ossicular bone over a biological conduction path, wherein the biological conduction path consists of biological components of the patient;
sensing in the implanted transducer an initial movement of the ossicular bone caused by the input provided over the biological conduction path;
obtaining an electrical signal output from the implanted transducer generated in response to sensing, in the implanted transducer, the initial movement of the ossicular bone; and,
utilizing the electrical signal output to determine diagnostic information relating to the patient, wherein said utilizing step comprises comparing the electrical signal output with a predetermined electrical signal output to generate the diagnostic information.

37. A method for obtaining diagnostic information relating to a patient having an implanted transducer, comprising:
vibrating an ossicular bone of the patient using an input provided to the ossicular bone over a biological conduction path, wherein the biological conduction path consists of biological components of the patient;

sensing in the implanted transducer an initial movement of the ossicular bone caused by the input provided over the biological conduction path;
obtaining an electrical signal output from the implanted transducer generated in response to sensing, in the implanted transducer, the initial movement of the ossicular bone; and,
utilizing the electrical signal output to determine diagnostic information relating to the patient, wherein said utilizing step comprises comparing the electrical signal output with a predetermined range of electrical signal outputs to generate the diagnostic information.

38. A method for obtaining diagnostic information relating to a patient having an implanted transducer, comprising:
vibrating an ossicular bone of the patient using an input provided to the ossicular bone over a biological conduction path, wherein the biological conduction path consists of biological components of the patient;
sensing in the implanted transducer an initial movement of the ossicular bone caused by the input provided over the biological conduction path;
obtaining an electrical signal output from the implanted transducer generated in response to sensing, in the implanted transducer, the initial movement of the ossicular bone; and,
utilizing the electrical signal output to determine diagnostic information relating to the patient, wherein said utilizing step further comprises:
calculating a ratio between the input and the electrical signal output; and
comparing the ratio to a predetermined ratio to generate the diagnostic information.

39. A method for obtaining diagnostic information relating to a patient having an implanted transducer, comprising:
vibrating an ossicular bone of the patient using an input provided to the ossicular bone over a biological conduction path, wherein the biological conduction path consists of biological components of the patient;
sensing in the implanted transducer an initial movement of the ossicular bone caused by the input provided over the biological conduction path;
obtaining an electrical signal output from the implanted transducer generated in response to sensing, in the implanted transducer, the initial movement of the ossicular bone; and,
utilizing the electrical signal output to determine diagnostic information relating to the patient, wherein said utilizing step further comprises:
obtaining at least one signal value from the electrical signal output; and
comparing the at least one signal value with a corresponding predetermined value to obtain comparison data, wherein the comparison data is indicative of the diagnostic information.

40. A method as recited in claim 39, wherein the at least one signal value corresponds with a magnitude component of the electrical signal output.

41. A method as recited in claim 40, wherein the input comprises at least one component of a predetermined frequency, and wherein the magnitude component of the electrical signal output is obtained in corresponding relation to the predetermined frequency of the input component.

42. A method as recited in claim 39, wherein the at least one signal value corresponds with a flow component of the electrical signal output.

43. A method for obtaining diagnostic information relating to a patient having an implanted transducer, comprising:
vibrating an ossicular bone of the patient using an input provided to the ossicular bone over a biological conduction path, wherein the biological conduction path consists of biological components of the patient;
sensing in the implanted transducer an initial movement of the ossicular bone caused by the input provided over the biological conduction path;
obtaining an electrical signal output from the implanted transducer generated in response to sensing, in the implanted transducer, the initial movement of the ossicular bone; and,
utilizing the electrical signal output to determine diagnostic information relating to the patient, wherein said utilizing step further comprises:
repeating the vibrating, sensing, obtaining, and utilizing steps in connection with each of a plurality of patient assessments conducted as spaced timed intervals to obtain a corresponding plurality of comparison data; and
utilizing the plurality of comparison data to generate the diagnostic information as a function of time.

* * * * *